(12) United States Patent
McFarlane

(10) Patent No.: US 7,316,699 B2
(45) Date of Patent: Jan. 8, 2008

(54) INTRODUCER ASSEMBLY FOR MEDICAL INSTRUMENTS

(75) Inventor: Richard H. McFarlane, Singer Island, FL (US)

(73) Assignee: Teleflex Medical Incorporated, Limerick, PA (US)

(*) Notice: Subject to any disclaimer, the term of this patent is extended or adjusted under 35 U.S.C. 154(b) by 607 days.

(21) Appl. No.: 10/360,550

(22) Filed: Feb. 7, 2003

(65) Prior Publication Data

US 2003/0171713 A1    Sep. 11, 2003

Related U.S. Application Data

(60) Provisional application No. 60/357,663, filed on Feb. 8, 2002.

(51) Int. Cl.
*A61B 17/32* (2006.01)

(52) U.S. Cl. .............. 606/168; 604/93.01; 604/164

(58) Field of Classification Search ........... 606/108, 606/168; 604/93.01, 178, 164.01–164.05
See application file for complete search history.

(56) References Cited

U.S. PATENT DOCUMENTS

| | | | |
|---|---|---|---|
| 3,176,690 A | 4/1965 | H'Doubler | |
| 4,193,399 A | 3/1980 | Robinson | |
| 4,230,110 A | 10/1980 | Beroff | |
| 4,617,933 A | 10/1986 | Hasson | |
| 4,642,101 A | 2/1987 | Krolikowski et al. | |
| 5,002,557 A | 3/1991 | Hasson | |
| 5,116,357 A | 5/1992 | Eberbach | |
| 5,176,697 A | 1/1993 | Hasson et al. | |
| 5,217,466 A | 6/1993 | Hasson | |
| 5,306,290 A | 4/1994 | Martins et al. | |
| 5,324,270 A | 6/1994 | Kayan et al. | |
| D354,562 S | 1/1995 | Medema | |
| 5,462,108 A * | 10/1995 | Katoh et al. ............. | 164/98 |
| 5,580,344 A | 12/1996 | Hasson | |
| 5,634,911 A | 6/1997 | Hermann et al. | |
| 5,634,937 A | 6/1997 | Mollenauer et al. | |
| 5,741,234 A | 4/1998 | Aboul-Hosn | |
| 5,782,813 A | 7/1998 | Yoon | |
| 5,830,232 A | 11/1998 | Hasson | |
| 5,871,474 A | 2/1999 | Hermann et al. | |
| 5,906,595 A * | 5/1999 | Powell et al. ......... | 604/167.01 |
| 5,964,781 A | 10/1999 | Mollenauer et al. | |
| 5,980,493 A | 11/1999 | Smith et al. | |
| 5,984,948 A | 11/1999 | Hasson | |
| 5,997,515 A * | 12/1999 | de la Torre et al. ...... | 604/256 |
| RE36,702 E | 5/2000 | Green et al. | |
| 6,077,249 A * | 6/2000 | Dittrich et al. ......... | 604/167.03 |
| 6,328,757 B1 | 12/2001 | Matheny | |

* cited by examiner

*Primary Examiner*—Michael J. Hayes
*Assistant Examiner*—Victor Nguyen
(74) *Attorney, Agent, or Firm*—Baker & Hostetler LLP

(57) ABSTRACT

An assembly structured to introduce a trocar or other medical instrumentation into a body cavity through an entry site formed in the cavity wall. The introducer assembly includes a base formed of a semi-rigid, flexible and/or a semi-flexible material having an instrument receiving passage extending there through, and further including an exterior sealing surface extending between proximal and distal portions of the base. The sealing surface has a predetermined configuration which is shaped to conform to the shape of the entry site as the base passes into the entry site. A fluid restricting seal is thereby established between the exterior of the base and the peripheral tissue surrounding the entry site, particularly when the entry site is formed by an incision commonly utilized an open laparoscopic procedure.

21 Claims, 1 Drawing Sheet

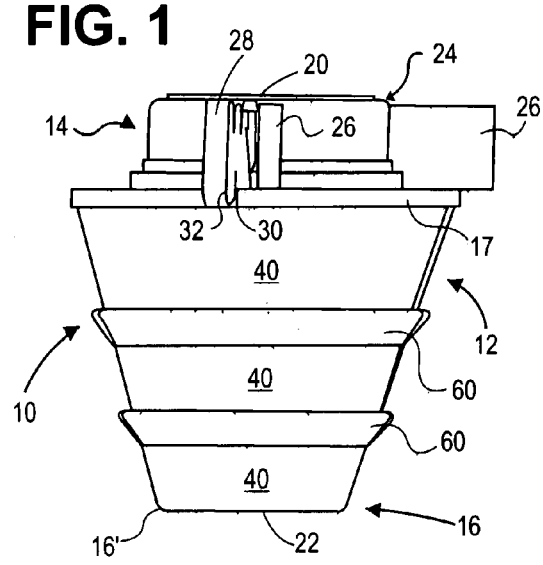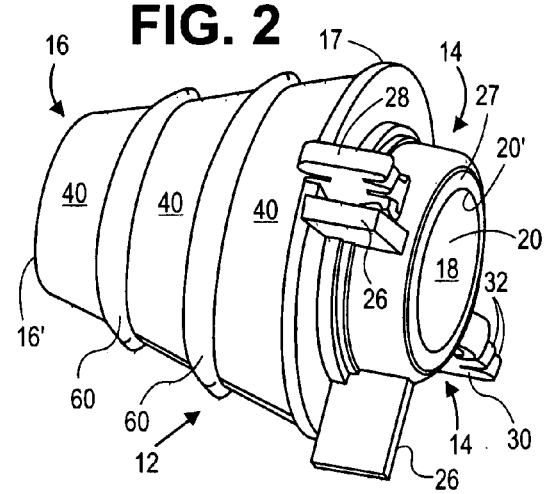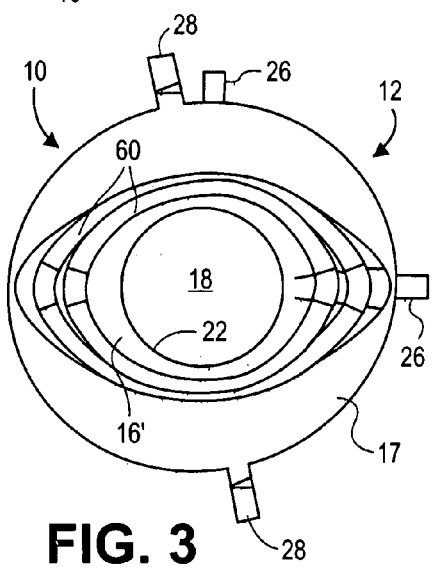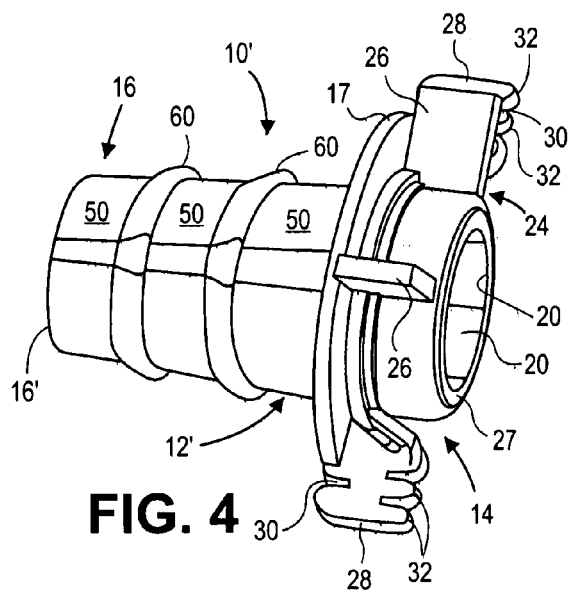

INTRODUCER ASSEMBLY FOR MEDICAL INSTRUMENTS

CLAIM OF PRIORITY

The present application is based on and a claim to priority is made under 35 U.S.C. Section 119(e) to provisional patent application currently pending in the U.S. Patent and Trademark Office having Serial No. 60/357,663 and a filing date of Feb. 8, 2002.

BACKGROUND OF THE INVENTION

1. Field of the Invention

This invention relates to an assembly for introducing and stabilizing a trocar or other medical instrument preferably, but not exclusively, during an open laparoscopic surgical procedure and includes a base having a sealing surface formed on the exterior thereof. The sealing surface comprises a predetermined cross-sectional configuration which is shaped to dilate and/or substantially conform to the resulting shape of an incision type entry site and thereby facilitate sealing engagement between the sealing surface of the base and the anatomical tissue contiguous to the entry site.

2. Description of the Related Art

For many years, laparoscopic surgery has been used on patients, when applicable, in order to avoid the serious and significant disadvantages generally associated with open surgery. Open surgery, as is generally recognized, requires that large incisions be made on a patient's body in order to more completely open a body cavity and allow the surgeon clear access to the organs or anatomical tissue involved. In contrast, laparoscopic surgical techniques involve the use of small diameter, long handled instruments including forceps, scissors, retractors, dissectors, etc. which are specifically designed and structured to be inserted through a small "entry site" formed in the wall of the body cavity being entered. Further, in order to more clearly observe the interior of the body cavity and the anatomical tissue or organs involved in the surgical procedure, an endoscopic camera or endoscope passes through the entry site to allow the medical personnel to view the interior portions on a monitor or other display facility. There are obvious advantages of endoscopic or laparoscopic surgery over the aforementioned open surgery technique based upon the minimally invasive procedures utilized on the patient.

Once the entry site has been prepared and access to the intended body cavity has been obtained, a trocar, cannula or like device is positioned into the entry site in order that the aforementioned types of laparoscopic instruments may be readily positioned into the interior of the body cavity and in operative contact with the organ or bodily tissue involve in the surgical procedure. Prior to conducting the intended surgical procedures involved, the body cavity is expanded so as to enlarge the working space for the surgeon, by insufflation. Insufflation is a process of injecting gas into the body cavity in order to create an expanded chamber at least partially filled with gas. In order to maintain the expanded area of the body cavity and facilitate the surgical procedure, the trocar assembly, cannula or an introducer device must be designed and structured to reduce the leakage of the insufflating gas from the entry site.

The more commonly used laparoscopic surgical techniques typically involve creating an entry site utilizing a sharpened point or bladed obturator which essentially "punctures" the anatomical tissue defining the surrounding wall of the body cavity being entered. In doing so, it is not uncommon to cause damage to interior organs or other anatomical tissue including blood vessels or the like. In certain instances, such damage can be significant, e.g., can lead to infection, and may result in severe trauma or death to the patient. The formation of the entry site in this manner is generally referred to as a "closed" laparoscopic technique.

However, in 1971 a doctor named Harrith Hasson of Chicago, Illinois developed a method of forming the entry site for the body cavity which is now referred to as the "open laparoscopic" technique. The purpose of the Hasson method is to eliminate or significantly reduce severe damage to the patient caused by the forced entry or puncture of an obturator or like entry instrument through the wall of the body cavity. In the Hasson technique, various medical instruments including a scalpel, scissors, retractors, etc. are used to carefully dissect each layer of the anatomical tissue associated with the cavity wall, thereby forming the entry site in a precise, controlled and safe manner. Once the entry site is so formed, a blunt headed trocar is inserted therethrough and the insufflation of the body cavity takes place.

While not initially accepted in the medical profession, in 1997 the Hasson method or technique was compared with the more commonly used, "closed" laparoscopic technique. Specifically, 489,000 closed laparoscopic and 12,400 open laparoscopic procedures were compared in a study conducted in the Netherlands. The Hasson method was shown to reduce laparoscopic access related injuries significantly. More specifically, injuries to organs was reduced by almost 50% and no patient suffered a single blood vessel injury. The study, therefore, concluded that the open laparoscopic method of access or entry site formation be advocated when minimally invasive surgical techniques are applicable, because it is safer than the more commonly used closed method.

However, and as set forth above, utilization of the Hasson method involves the formation of an "incision type" of entry site. Accordingly, the entry site so formed has an at least partially elongated shape or configuration, like a "slit." As such, the insertion of a commonly structured introducer device into the entry site may result in a greater tendency of leakage of the insufflating gas. More specifically, conventionally structured introducer instruments or devices are typically configured to be entirely round or circular and are thought by the inventor herein to be more susceptible to gas leaks about the exterior surface thereof. As a result it is difficult, if not impossible, to maintain the insufflated state of the abdomen, i.e., the preferred, expanded work area within the body cavity.

Accordingly, because of the increased acceptance of the Hasson method of open laparoscopic surgery there is a need for an improved introducer assembly. Any such introducer assembly developed would preferably be designed and structured to restrict the leakage of insufflating gas from the body cavity during the introduction of medical instruments, as well as during the entire surgical procedure. Any such improved introducer assembly developed should also be capable of being securely anchored and maintained in its intended position at and/or within the entry site and further, include structure specifically designed to define or create a fluid type seal between exterior portions of the improved introducer assembly and the anatomical tissue contiguous to the entry site, particularly of the type formed by the Hasson method. Any such improved introducer assembly should be structured to be used specifically, but not exclusively, with an open laparoscopic technique. In doing so, the disadvantages of true open surgery as well as problems associated with laparoscopic access related injuries would be significantly reduced.

SUMMARY OF THE INVENTION

The present invention is directed to an introducer assembly structured to introduce and stabilize a trocar (and possibly other medical instruments) of the type typically used in endoscopic or laparoscopic surgical procedures, within a body cavity through a pre-formed entry site. In addition, the introducer assembly of the present invention is structured to sealing engage the anatomical tissues surrounding and/or contiguous to the entry site in order to restrict the escape of insufflating gas typically introduced into the body cavity to cause its expansion, and thereby, enlarge the work area for the surgeon.

More specifically, the introducer assembly of the present invention comprises a base preferably formed of a semi-rigid, semi-flexible and/or even flexible material having sufficient structural integrity to at least partially maintain a predetermined configuration in order to establish the aforementioned sealing engagement with the surrounding anatomical tissue. The rigidity or structural integrity of the base should also be sufficient to facilitate the stabilization of a trocar or other instrument passing through the base into the body cavity.

Accordingly, when the base is in its intended position within the entry site, a proximal portion thereof is located exteriorly of the body cavity. The base also comprises a distal portion disposed closely adjacent and/or possibly partially within the body cavity, and as such, is oppositely disposed to the proximal portion. The base further includes a passage formed on the interior thereof. The passage includes an open proximal end disposed adjacent to the proximal portion of the base and an open distal end disposed adjacent to the distal portion and extending through a distal extremity thereof. The passage and the open proximal and distal ends are specifically dimensioned and configured to allow the placement there through of a trocar or other medical instrument utilized in the performance of the intended surgical procedure.

Another feature of the various preferred embodiments of the present invention includes the provision of a sealing surface formed on the exterior of the base. The sealing surface extends along at least a portion of the base and preferably, but not necessarily, along at least a majority of the distance between the proximal portion and the distal portion. Moreover, the sealing surface comprises a predetermined transverse cross-sectional configuration shaped to substantially conform to the overall shape or configuration of the entry site. Also, in order to be readily adaptive to any orientation of the base within the entry site, the predetermined cross-sectional configuration of the sealing surface is substantially continuous along its length as it extends between the proximal and distal ends of the base.

As set forth above, there is a lower incidence of damage to the internal organs or other anatomical tissue of the patient when using the "open laparoscopic" procedure than when using the closed laparoscopic procedure. As such, the aforementioned Hasson method involves the creation of the entry site by forming an at least partially elongated incision through the various layers of the anatomical tissue associated with the wall of the body cavity being entered. This incision type entry site differs from the "puncture-type" entry site formed by an obturator associated with a conventional trocar assembly. Therefore, the cross-sectional configuration of the sealing surface, exteriorly formed on the base, also has a predetermined, substantially elongated and preferably oval or elliptical transverse cross-sectional configuration, extending substantially continuously along its length. The predetermined, preferably oval transverse cross-sectional configuration of the sealing surface substantially conforms to the shape of the incision type entry site and thereby facilitates the formation of a "skin seal" with the various anatomical tissues contiguous to the periphery of the incision or entry site.

In order to further facilitate the establishment and maintenance of a fluid tight seal at the entry site, a most preferred embodiment of the present invention comprises the base and the sealing surface having a substantially conical configuration extending between the distal portion and the proximal portion. The term "substantially conical" as used herein is meant to include a frusto-conical configuration, as described in greater detail hereinafter. In addition, in order to facilitate the accurate, operative placement of the base into the entry site, the aforementioned extremity of the distal portion comprises a round or circular configuration to facilitate the entry of the distal portion of the base into the entry site. This round or circular configuration of the distal extremity of the base transitions into the aforementioned elongated, predetermined cross-sectional configuration of the sealing surface, preferably defined by the aforementioned oval or elliptical shape, and further, should aid with sealing against the outer diameter of the trocar or other instrument with which the device is used.

Other structural features of the various preferred embodiments of the introducer assembly of the present invention comprise an anchoring assembly. The anchoring assembly includes at least one, but preferably a plurality of projections spaced from one another and extending radially outward from the proximal portion of the base. Each of the one or more projections or "ears" are disposed and structured to facilitate the suturing of the base to the anatomical tissue in which the entry site is formed. The base is thereby maintained in its intended, operative position within the entry site until intentionally removed by the attending medical personnel.

In at least one preferred embodiment of the present invention, the base also includes a retaining assembly including one or more retaining ribs formed on the exterior sealing surface and extending outwardly therefrom. Each of the one or more retaining ribs are annular, and more specifically, are defined by a continuous, closed configuration disposed at different spaced locations along the sealing surface. Therefore, the retaining ribs are disposed and structured to resist inadvertent removal of the base from the entry site, and further, may further serve to maintain the seal between the assembly and the anatomical tissues surrounding it. However, intended forced removal of the base is readily accomplished after the surgical procedure has been completed and upon removal of the sutures from the aforementioned anchoring assembly.

Yet another structural feature associated with the introducer assembly of the present invention is the provision of a connecting assembly mounted on the base in communicating relation with the interior passage extending there through. The connecting assembly is cooperatively structured so as to selectively vary the size of the interior passage formed within the base. In doing so, a trocar or other instrument passing through the interior passage is thereby effectively gripped such that the instrument is removably connected to the base. Such gripping or connection will further facilitate the stabilization of the instrument being introduced through the entry site, while not interfering with the intended positioning or manipulation instrument during the performance of the surgical procedure.

As set forth above, a most preferred embodiment of the present invention comprises the transverse cross-sectional configuration of the sealing surface being somewhat elongated and/or oval in shape so as to conform to the typically elongated, incision-type entry site. However, it should be noted that the aforementioned elongated, predetermined cross-sectional configuration of the sealing surface is not meant to be limited to a precise oval or elliptical configuration but may vary therefrom in order to better conform to different shapes of an entry site. Moreover, in order to best facilitate the formation of a skin seal about the periphery of the entry site and thereby restrict the escape of insufflation gas between the exterior of the base and the periphery of the entry site, the overall dimension and configuration of the sealing surface including, but not necessarily limited to, its cross-sectional and/or longitudinal configurations should substantially conform to that of the entry site.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a front plan view of a preferred embodiment of the introducer assembly of the present invention.

FIG. 2 is a side view in perspective of the embodiment of FIG. 1.

FIG. 3 is a bottom view of the embodiment of FIGS. 1 and 2.

FIG. 4 is a side perspective view of yet another preferred embodiment of the introducer assembly of the present invention.

Like reference numerals refer to like parts throughout the several views of the drawings.

DETAILED DESCRIPTION OF THE PREFERRED EMBODIMENT

As shown in the accompanying drawings, the present invention is directed to an introducer assembly generally indicated as 10. The introducer assembly 10 is structured to facilitate the introduction of a trocar (and possibly other instruments) into the interior of a body cavity so as to perform laparoscopic or endoscopic surgery on various organs or tissues within the body cavity. More specifically, the introducer assembly 10 is positioned and maintained within an entry site preferably formed by an incision through the layers of anatomical tissue of the wall of the body cavity. Once so positioned, the introducer assembly 10 is structured to restrict the inadvertent escape or leakage of insufflating gases through the entry site. The insufflation of gas into the body cavity is, of course, a commonly used technique in laparoscopic surgery to expand the interior of the cavity and thereby provide the surgeon with better access.

With primary reference to the most preferred embodiment of the present invention as shown in FIGS. 1 through 3, the introducer assembly 10 comprises a base generally indicated as 12 having a proximal portion 14 and a distal portion 16. When in its intended, operative position, the distal portion 16 is disposed through the entry site and into adjacent relation to the interior of the body cavity, although perhaps in a few patients, it may be extend into the body cavity. The proximal portion 14 is disposed exteriorly of the body cavity and is readily accessible so as to facilitate the introduction of the trocar assembly or other instrumentation into the body cavity. The medical instruments are positioned into the body cavity by the inclusion of a passage 18 extending through the interior of the base 12. The passage 18 terminates in an open proximal end 20 and an oppositely disposed open distal end 22. The dimension and configuration of the passage 18, as well as the open proximal and distal ends 20 and 22 are sufficient to facilitate the entry and removal of a trocar assembly and/or other instruments completely through the base 12 and into and out of the body cavity.

The base 12 of the introducer assembly 10 of the various preferred embodiments of the present invention may be formed of a semi-rigid and/or semi-flexible and/or flexible material. For example, the proximal portion 14 is preferably formed of a rigid and/or semi-rigid material, such as but not limited to hard plastic material, so as to provide sufficient structural integrity to facilitate the stabilization of a trocar or other instrument passing through the base 12 and into the body cavity, even upon manipulation thereof. Also, at least a part of, but preferably all, the distal portion 16 of the base may be formed of a flexible or semi-flexible material. Further, the material from which the distal portion 16, as well as other tissue contacting portions of the base, is formed should also have sufficient structural integrity to maintain an overall configuration suited to establish the aforementioned sealing engagement with the surrounding anatomical tissue at the entry site. For instance, the distal portion 16 may be formed of a silicone material (in whole or in part) or silicon like material which may be in the range of generally about 50 durometers, versus the highly flexible 10 durometers on the one hand and more rigid 80 durometers on the other, on that scale known to those of skill in the art working with silicone and like materials.

Additional structural features of the various preferred embodiments of the introducer assembly 10 include the provision of a connecting assembly generally indicated as 24. The connecting assembly 24 is movably mounted or secured to the base 12 preferably, but not exclusively, adjacent the proximal portion 14. In one preferred embodiment of the introducer assembly 10, the connecting assembly 24 comprises at least one, but preferably two outwardly extending flanges 26. One or both of the flanges 26 are movable on or relative to the base and one another so as to regulate the interior dimension of the opening 18' of the interior passage 18, which is formed in the open proximal end 20. More specifically, manipulation of one or both of the flanges 26 will provide for a selective positioning of one or more gripping members 27 into and out of a constricting or gripping orientation about the periphery of the opening 18' as disclosed in FIG. 2. As such, the one or more gripping members 27 may constrict the diameter of the opening 18' until an instrument inserted within the passage 18 is engaged and thereby stabilized by the one or more gripping members 27. The gripping member(s) 27 may assume a variety of different structural configurations, such as being at least partially annular and including one or more segments movable relative to one another and the base 12 so as to constrict the interior of the opening 20' about the inserted instrument. Further, the medical instrument disposed within the passage 18 may be removably gripped and stabilized in a manner which still allows it to be moved within an intended range of motion, once the instrument is introduced into the body cavity. It is emphasized that a variety of other connecting assemblies could be utilized and included in the introducer assembly 10 for purposes of stabilizing the instruments disposed within the passage 18.

Yet another structural feature included in at least some of the various preferred embodiments of the present invention is an anchoring assembly. The anchoring assembly comprises at least one, but preferably a plurality of projections or "ears" 28 connected to the base 12 substantially adjacent to the proximal portion 14. More specifically, the one or more anchoring projections 28 are spaced from one another about the circumference of the proximal portion 14. In addition the anchoring projections extend radially outward from the proximal portion in at least partially overlying relation to the exposed skin or other anatomical tissue in which the incision of the entry site is formed. As such, each of the projections 28 are disposed and structured to facilitate the "anchoring" of the introducer assembly 10 to the body of the patient so that the base 12 is securely retained within the entry site as intended. Moreover, each of the one or more anchoring projections 28 comprise a plurality of spaced apart slots and alternating ribs 30 and 32 respectively, which are structured to accommodate the placement sutures thereon and thereby facilitate the suturing of the base 12 to the anatomical tissue surrounding the entry site. Upon the intended removal of the base 12 from the entry site, the sutures serving to anchor the base 12 by means of their connection to the anchoring projections 28 are easily removed.

Yet another structural feature of the various preferred embodiments of the present invention is the provision of a sealing surface, generally indicated as 40 and integrally formed on and thereby defining the exterior of at least a majority of the base 12. The sealing surface 40 preferably extends between and along at least a majority of the distance between the distal portion 16 and the proximal portion 14. In the embodiment of FIGS. 1 through 3, the sealing surface 40 extends between a position contiguous to an extremity 16' of the distal portion 16 and a flange, stop or barrier structure 17 located adjacent or associated directly with the proximal portion 14. Accordingly, the sealing surface 40 is disposed and configured to facilitate the forming of a fluid flow restricting seal between the anatomical tissue surrounding the entry site and the sealing surface 40 itself. As such the sealing surface 40, and accordingly, a significant portion of the base 12 comprise a predetermined cross-sectional configuration as best shown in FIG. 3.

In a most preferred embodiment, the cross-sectional configuration of the sealing surface 40 has a substantially elongated transverse configuration which at least partially conforms to and/or corresponds with that of an incision, i.e., an entry site that is generally elongated or slit-like. As is known in the medical profession, the "open laparoscopic" technique was initially developed by Dr. Harrith Hasson of Chicago, Ill. As such, the entry site, instead of being formed by sharpened point or bladed obturator associated with a trocar, is more conventionally formed as an incision, using a scalpel, scissors, etc. These instruments are used to carefully dissect each layer of tissue until the entry site is formed and communication with the interior of the body cavity has been established. As a result, the "Hasson technique" results in the formation of an at least partially elongated incision-type entry site.

Accordingly, the sealing surface 40 has a predetermined substantially elongated transverse cross-sectional configuration, along its length, which substantially conforms to the resulting shape of the entry site upon the base 12 being inserted in and/or dilating the entry site. Therefore the conforming of the configuration and dimension of the sealing surface 40 to the entry site is at least sufficient to form a fluid restricting seal between the skin or tissue surrounding the entry site and the exterior of the base 12. In a most preferred embodiment, the substantially elongated transverse configuration of the sealing surface 40 is in the form of an oval or elliptical shape, thereby further facilitating sealing engagement with the periphery of the entry site and/or the anatomical tissue contiguous thereto. However, while the transverse cross-sectional configuration of the sealing surface is substantially elongated and/or preferably oval as set forth above, at least one preferred embodiment of the present invention includes the distal extremity 16' having a substantially circular or rounded shape. This preferably rounded shape may facilitate entry of the base 12 into the entry site and aid with sealing against the outer diameter of the trocar or other instrument.

Further, the transverse cross-sectional configuration of the sealing surface 40 extends substantially along the length of the sealing surface 40. As used herein, the "length" of the sealing surface 40 may be defined by at least a portion of the distance, or preferably at least a majority of the distance, between the distal portion 16 and/or the extremity 16' and the proximal portion 14 and/or the flange or barrier 17 associated therewith. Also, in the most preferred embodiment of FIGS. 1 through 3 a further structural feature of the sealing surface 40 and of the base 12 comprises the longitudinal configuration thereof having a substantially conical or more accurately "frusto-conical" configuration.

The preferred embodiments of FIGS. 1 through 4 also include the provision of a plurality of retaining ribs 60, as will be discussed in greater detail hereinafter. As disclosed herein, the ribs 60 are spaced from one another and extend radially outward from the sealing surface 40. As such it is recognized the while the sealing surface 40 may be accurately described as extending substantially continuously along at least a portion of the base 12, between the proximal and distal portions 14 and 16, this description is meant to include the one or more ribs 60 being positioned as shown in the accompanying Figures.

With primary reference to FIG. 4, yet another preferred embodiment of the present invention comprises the introducer assembly 10' including a base 12' having a sealing surface 50 integrally formed on the exterior thereof. As with the embodiment of FIGS. 1 through 3, the sealing surface 50 extends along at least a portion of the length of the base 12' between the distal portion 16 and/or distal extremity 16' and the proximal portion 14 and/or barrier flange 17. Also, as clearly represented in FIG. 4, the sealing surface 50 comprises a longitudinal configuration substantially in the form of a cylinder as versus the conical or frusto-conical, longitudinal configuration of the introducer assembly 10, of the embodiment of FIGS. 1 through 3.

However, it should be noted that although the longitudinal configuration of the sealing surface 50 is substantially cylindrical, as versus substantially conical, the transverse, cross-sectional configuration thereof still defines a substantially elongated, predetermined configuration which conforms to the at least partially elongated configuration of an incision type entry site, especially once the entry site is dilated. As such, the transverse, cross-sectional configuration of the sealing surface 50 also comprises a substantially oval or elliptical shape similar to that shown in FIG. 3. Also, the distal extremity 16' of base 12' also preferably includes the aforementioned circular or rounded configuration so as to facilitate initial entry of the base 12' into the entry site.

Yet another structural feature of each of the preferred embodiments of FIGS. 1 through 4 is the provision of a retaining assembly comprising at least one, but preferably a plurality of retaining members or ribs 60. Each of the retaining ribs 60 comprises a substantially annular configuration further defined by a continuous, closed shape. Further, the plurality of ribs 60 are disposed in spaced, substantially parallel relation to one another as clearly depicted in FIGS. 1 through 4. The structure of ribs 60 are likely to aid with maintaining the seal as well, and further, the position and structure of the plurality of retaining ribs 60 are such as to facilitate retention of the base 12 and 12', and in particular, the respective sealing surfaces 40 and 50 of the introducer assemblies 10 and 10' into a preferred, sealing engagement with anatomical tissue contiguous to the incision type entry site, as set forth above. It should be noted however, that once the sutures are removed from the anchoring projections 28, the respective introducer assemblies 10 and 10' can be withdrawn from the entry site in which it is placed.

Since many modifications, variations and changes in detail can be made to the described preferred embodiment of the invention, it is intended that all matters in the foregoing description and shown in the accompanying drawings be interpreted as illustrative and not in a limiting sense. For example, while the present invention has been described primarily as working in the environment of trocars, it is understandable that the present invention may work with other medical instruments, whether now known or yet to be developed. Thus, the scope of the invention should be determined by the appended claims and their legal equivalents.

Now that the invention has been described,

What is claimed is:

1. An assembly structured to introduce medical instruments into a body cavity through an entry site, said assembly comprising:
   a) a base disposable within the entry site and including a proximal portion and a distal portion, said proximal portion disposed in an accessible location from an exterior of the body cavity,
   b) a passage extending through said base between said proximal and distal portions and dimensioned to receive the instrument therethrough,
   c) said base including an exterior sealing surface having a transverse cross-section of predetermined configuration substantially conforming to a configuration of the entry site,
   d) said predetermined configuration is elongated in substantial conformance with an elongated incision defining the entry site and comprises a substantially oval configuration, and
   e) said sealing surface disposable in sealing engagement with the entry site; wherein further comprising a retaining assembly formed on said sealing surface and disposed and structured to retain said base within the entry site; and wherein said retaining assembly comprises at least one rib extending outwardly from said sealing surface.

2. An assembly as recited in claim 1 wherein said predetermined configuration of said sealing surface extends along at least a majority of a length of said sealing surface between said proximal and distal portions.

3. An assembly as recited in claim 2 wherein said sealing surface further comprises a longitudinal configuration which is substantially cylindrical along said base between said proximal and distal portions.

4. An assembly as recited in claim 2 wherein said sealing surface further comprises a longitudinal configuration which is substantially conical along said base between said proximal and distal portions.

5. An assembly as recited in claim 1 wherein said sealing surface further comprises a longitudinal configuration which is substantially cylindrical along said base between said proximal and distal portions.

6. An assembly as recited in claim 1 wherein said sealing surface further comprises a longitudinal configuration which is substantially conical along said base between said proximal and distal portions.

7. An assembly as recited in claim 1 wherein said distal portion comprises a distal extremity including a substantially round transverse cross-sectional configuration.

8. An assembly as recited in claim 7 wherein said distal portion includes an opening communicating with said passage and extending through said distal extremity.

9. An assembly as recited in claim 1 wherein said base and said sealing surface are at least partially formed of a semi-flexible material.

10. An assembly as recited in claim 1 wherein said base and said sealing surface are at least partially formed of a substantially rigid material.

11. An assembly as recited in claim 1 wherein said retaining assembly comprises a plurality of ribs formed on said sealing surface in spaced relation to one another.

12. An assembly as recited in claim 11 wherein each of said plurality of ribs comprises an at least partially closed, substantially continuous configuration conforming to said transverse cross-sectional configuration of said sealing surface.

13. An assembly as recited in claim 1 further comprising a connecting assembly mounted on said base and structured to selectively and removably secure said base to an instrument within said passage.

14. An assembly as recited in claim 1 further comprising an anchoring assembly secured to said base and disposed and structured to facilitate suturing of said base to an area adjacent the entry site.

15. An assembly as recited in claim 14 wherein said anchoring assembly comprises at least one projection extending radially outward from said proximal portion, said projection disposed and configured to be sutured to anatomical tissue adjacent said entry site.

16. An assembly as recited in claim 14 wherein said anchoring assembly comprises a plurality of projections disposed in spaced relation to one another and extending radially outward from said proximal portion, each of said plurality of projections structured to be sutured to anatomical tissue adjacent said entry site.

17. An assembly structured to introduce a medical instrument to a body cavity through an entry site, said assembly comprising:
   a) a base disposable within the entry site and including a proximal portion and a distal portion, said proximal portion accessible from an exterior of the body cavity,
   b) a passage extending through said base between said proximal and distal portions and dimensioned to receive an instrument therethrough,
   c) said base including a sealing surface formed on an exterior thereof and disposed between said proximal and distal portions,
   d) said sealing surface comprising a transverse cross-section having a substantially elongated configuration comprising a substantially oval shape extending along at least the majority of a length of said sealing surface, and
   e) said elongated configuration shaped to substantially conform to and facilitate sealing engagement of said sealing surface with an elongated incision type entry site; wherein further comprising a retaining assembly formed on said sealing surface and disposed and structured to retain said base within the entry site; and wherein said retaining assembly comprises at least one rib extending outwardly from said sealing surface.

18. An assembly as recited in claim 17 wherein said base comprises a substantially cylindrical configuration along the length of said sealing surface between said proximal and distal portions.

19. An assembly as recited in claim 17 wherein said base comprises a substantially frusto-conical configuration along the length of said sealing surface between said proximal and distal portions.

20. An assembly as recited in claim 17 wherein said distal portion comprises an extremity including a transverse configuration having a substantially round shape.

21. An assembly as recited in claim 17 further comprising an anchoring assembly formed adjacent said proximal portion and structured and disposed to facilitate suturing of said base to anatomical tissue adjacent the entry site.

* * * * *